(12) United States Patent
Freeman et al.

(10) Patent No.: US 7,749,197 B2
(45) Date of Patent: Jul. 6, 2010

(54) ELECTROACTIVE POLYMER-BASED PERCUTANEOUS ENDOSCOPY GASTROSTOMY TUBE AND METHODS OF USE

(75) Inventors: Lynetta Freeman, West Chester, OH (US); Mark S. Ortiz, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1377 days.

(21) Appl. No.: 11/161,265

(22) Filed: Jul. 28, 2005

(65) Prior Publication Data
US 2007/0038238 A1 Feb. 15, 2007

(51) Int. Cl.
*A61M 5/178* (2006.01)
(52) U.S. Cl. .................................. 604/164.01
(58) Field of Classification Search ............ 604/164.01, 604/533, 96.01
See application file for complete search history.

(56) References Cited

U.S. PATENT DOCUMENTS

| | | | | |
|---|---|---|---|---|
| 4,148,307 | A | * | 4/1979 | Utsugi .......................... 600/116 |
| 4,676,228 | A | * | 6/1987 | Krasner et al. ............... 600/116 |
| 5,337,732 | A | * | 8/1994 | Grundfest et al. ........... 600/116 |
| 5,527,280 | A | | 6/1996 | Goelz |
| 6,060,811 | A | * | 5/2000 | Fox et al. ..................... 310/311 |
| 6,249,076 | B1 | * | 6/2001 | Madden et al. .............. 310/363 |
| 6,376,971 | B1 | * | 4/2002 | Pelrine et al. ................ 310/363 |
| 6,514,237 | B1 | * | 2/2003 | Maseda ........................ 604/533 |
| 6,679,836 | B2 | * | 1/2004 | Couvillon, Jr. .............. 600/146 |
| 7,259,503 | B2 | * | 8/2007 | Pei et al. ...................... 310/363 |
| 7,353,747 | B2 | * | 4/2008 | Swayze et al. .................. 92/92 |
| 2003/0212306 | A1 | | 11/2003 | Banik |
| 2003/0225393 | A1 | * | 12/2003 | McMichael et al. .......... 604/513 |
| 2003/0229332 | A1 | * | 12/2003 | Intoccia ........................ 604/508 |
| 2003/0236531 | A1 | * | 12/2003 | Couvillon, Jr. .............. 606/113 |
| 2005/0085693 | A1 | | 4/2005 | Belson et al. |
| 2007/0025868 | A1 | * | 2/2007 | Swayze et al. ............... 417/474 |

FOREIGN PATENT DOCUMENTS

WO WO-2005/072809 8/2005

* cited by examiner

*Primary Examiner*—Nicholas D Lucchesi
*Assistant Examiner*—Diva Ranade

(57) ABSTRACT

Embodiments of the present invention generally provide methods and devices for providing percutaneous access to a tissue. In one exemplary embodiment, a PEG tube is provided having an elongate member with a proximal end adapted to be positioned adjacent to a tissue surface, a distal end adapted to be inserted through tissue, and an inner lumen extending between the proximal and distal ends and adapted to allow fluid flow there through. The PEG tube can also include an electrically actuatable element coupled to the distal end of the elongate member and configured to change dimensionally upon delivery of electrical energy thereto. In use, the electrically actuatable element can be adapted to expand to engage tissue and secure the distal end of the PEG tube to the tissue.

19 Claims, 11 Drawing Sheets

ELECTROACTIVE POLYMER-BASED PERCUTANEOUS ENDOSCOPY GASTROSTOMY TUBE AND METHODS OF USE

FIELD OF THE INVENTION

The present invention relates broadly to surgical devices, and in particular to methods and devices for securing a percutaneous endoscopic gastrostomy tube to a gastrointestinal location.

BACKGROUND OF THE INVENTION

In cases of severe obesity, patients can undergo various types of surgical procedures to tie off, staple, or bypass portions of the stomach and gastrointestinal tract (e.g., large intestine or small intestine). These procedures can reduce the amount of food desired and ingested by the patient, thereby causing the patient to lose weight.

One surgical procedure, known as a Roux-En-Y gastric bypass, creates a permanent surgical reduction of a patient's stomach volume and a bypass of the patient's intestine. In the procedure, the stomach is separated into a smaller, upper stomach pouch and a larger, lower stomach pouch, such as by using a stapling device. A segment of the patient's small intestine (e.g., a segment distal of the duodenum or proximal of the jejunum) is then brought from the lower abdomen and joined with the upper stomach pouch created through a half-inch opening, or stoma, in the stomach pouch and small intestine. This segment of the small intestine, known as the "Roux loop," carries food from the upper stomach pouch to the remainder of the intestines, where the food is digested. The remaining lower stomach pouch and the attached segment of duodenum are then reconnected to form another anastomotic connection to the Roux loop at a location approximately 50-150 cm (1.6-4.9 ft) from the stoma, typically using a stapling instrument. From this connection, digestive juices from the bypassed stomach (e.g., the lower stomach pouch), pancreas, and liver enter the jejunum or ileum to aid in digestion. The relatively small size of the upper stomach pouch therefore reduces the amount of food that the patient can eat at one time, thereby leading to weight loss in the patient.

While the Roux-En-Y gastric bypass procedure maintains oral access to the upper stomach pouch, the procedure eliminates oral access to the bypassed lower stomach. In certain cases, such as when a patient becomes ill following the Roux-En-Y gastric bypass, the patient can require either delivery of nutrients and fluids to the bypassed lower stomach pouch or removal of excess digestive juices from the bypassed lower stomach. To provide external access to the lower stomach pouch, a percutaneous endoscopic gastrostomy (PEG) tube can be inserted within the pouch.

Conventional PEG tubes include a flexible tube having a balloon positioned on a distal end of the tube. The PEG tube is implanted by inserting the distal end of the PEG tube through openings formed within the abdominal muscle wall of the patient and the lower stomach pouch to position the deflated balloon within the lower stomach pouch. The balloon is then inflated to engage the lower stomach pouch wall to secure the PEG tube to the stomach pouch. Fluids can then be introduced into or removed from the stomach pouch via the PEG tube.

In some Roux-En-Y gastric bypass procedures, the lower stomach pouch can be difficult to subsequently locate and access within the patient (e.g., at a time subsequent to the gastric bypass procedure). The PEG tube can thus also be used to reposition the lower stomach pouch in proximity to the abdominal wall. This can be achieved by pulling the flexible tube after the balloon is inflated to pull the lower stomach pouch toward the abdominal wall. Eventually, the adhesion will be formed between the lower stomach pouch and the abdominal wall to permanently anchor or secure the tissues to each other.

While the use of conventional PEG tubes can be an effective mechanism to deliver or withdraw fluids from the lower stomach pouch, or to position a lower stomach pouch relative to an abdominal wall, there are some drawbacks with current PEG tubes. For example, during operation of the PEG tube, the balloon should only be inflated to an amount that is necessary to engage the stomach pouch, as over inflation of the balloon can create excess pressure within the stomach. However, it may be necessary to inflate the balloon to an undesirably large size in order to allow the balloon to engage the stomach wall without passing through the opening. The use of a balloon can also pose the risk of over inflation leading to rupture or leakage during use, thereby limiting the ability for the PEG tube to maintain its anchored position within the lower stomach pouch.

Accordingly, there is a need for improved methods and devices for securing a PEG tube within a lower stomach pouch following a Roux-En-Y gastric bypass.

BRIEF SUMMARY OF THE INVENTION

The present invention generally provides methods and devices for providing percutaneous access to a body lumen. In one exemplary embodiment, a PEG tube is provided having an elongate member with a proximal end that is adapted to be positioned adjacent to a tissue surface, a distal end that is adapted to be inserted through tissue and into a body lumen, and an inner lumen extending between the proximal and distal ends and adapted to allow fluid flow there through. The PEG tube can also include an electrically expandable element coupled to the distal end of the elongate member configured to change dimensionally upon delivery of electrical energy thereto. In one embodiment, the electrically expandable element can be configured to radially expand upon delivery of electrical energy thereto.

In one embodiment, the PEG tube can have a first electrically expandable element coupled to the distal end of the elongate member and configured to change dimensionally upon delivery of electrical energy thereto. The PEG tube can also include additional expandable elements, such as a second electrically expandable element positioned just proximal to the first electrically expandable element to allow the first and second electrically expandable elements to engage tissue therebetween when energy is delivered thereto. A third electrically expandable element can optionally be coupled to the proximal end of the elongate member and configured to engage tissue to prevent passage of the proximal end of the PEG tube through tissue and into the body.

In yet another embodiment, a PEG tube is provided having a hollow elongate member with a proximal portion that is adapted to be positioned adjacent to a tissue surface and a distal portion that is adapted to be inserted through tissue. The PEG tube can further include at least one electroactive polymer actuator coupled to the hollow elongate member. A diameter of the electroactive polymer actuator can be adapted to be selectively increased when energy is delivered thereto to engage the tissue.

Methods for implanting a percutaneous endoscopic gastrostomy (PEG) tube are also provided. In one embodiment, the method can include inserting a distal portion of a PEG tube through tissue and into a body lumen to position an expandable element coupled to the distal portion of the PEG tube within the body lumen. The method can further include delivering an amount of energy to the expandable element to increase a size of the expandable element, thereby causing the expandable element to engage the body lumen. In certain exemplary embodiments, energy can be delivered in an amount that correlates to a desired size of the expandable element. The method can also optionally include retracting the PEG tube to move the tissue engaged by the expandable element.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with features of other embodiments. Such modifications and variations are intended to be included within the scope of the present invention.

The present invention generally provides methods and devices for providing percutaneous access to a body lumen. In an exemplary embodiment, a PEG tube is provided having an elongate member with a proximal end adapted to be positioned adjacent to a tissue surface or otherwise external to a patient's body, a distal end adapted to be inserted through tissue and into a body lumen or organ, and an inner lumen extending between the proximal and distal ends and adapted to allow fluid flow therethrough. The PEG tube can also include an expandable element coupled to the distal end of the elongate member and configured to change dimensionally upon delivery of electrical energy thereto. In use, the expandable element can be positioned within a body lumen, e.g., the stomach or other organ, and expanded to engage tissue, thereby securing the distal end of the PEG tube within the lumen. Fluids can then be introduced into and/or removed from the PEG tube. A person skilled in the art will appreciate that the device can include any combination of electrically expandable elements and non-electrically expandable elements or other features to secure the PEG tube to tissue. A person skilled in the art will also appreciate that, while the device is described for use in a Roux-En-Y gastric bypass procedure, the device can be used in a variety of surgical procedures for a variety of purposes.

Figure 1A:
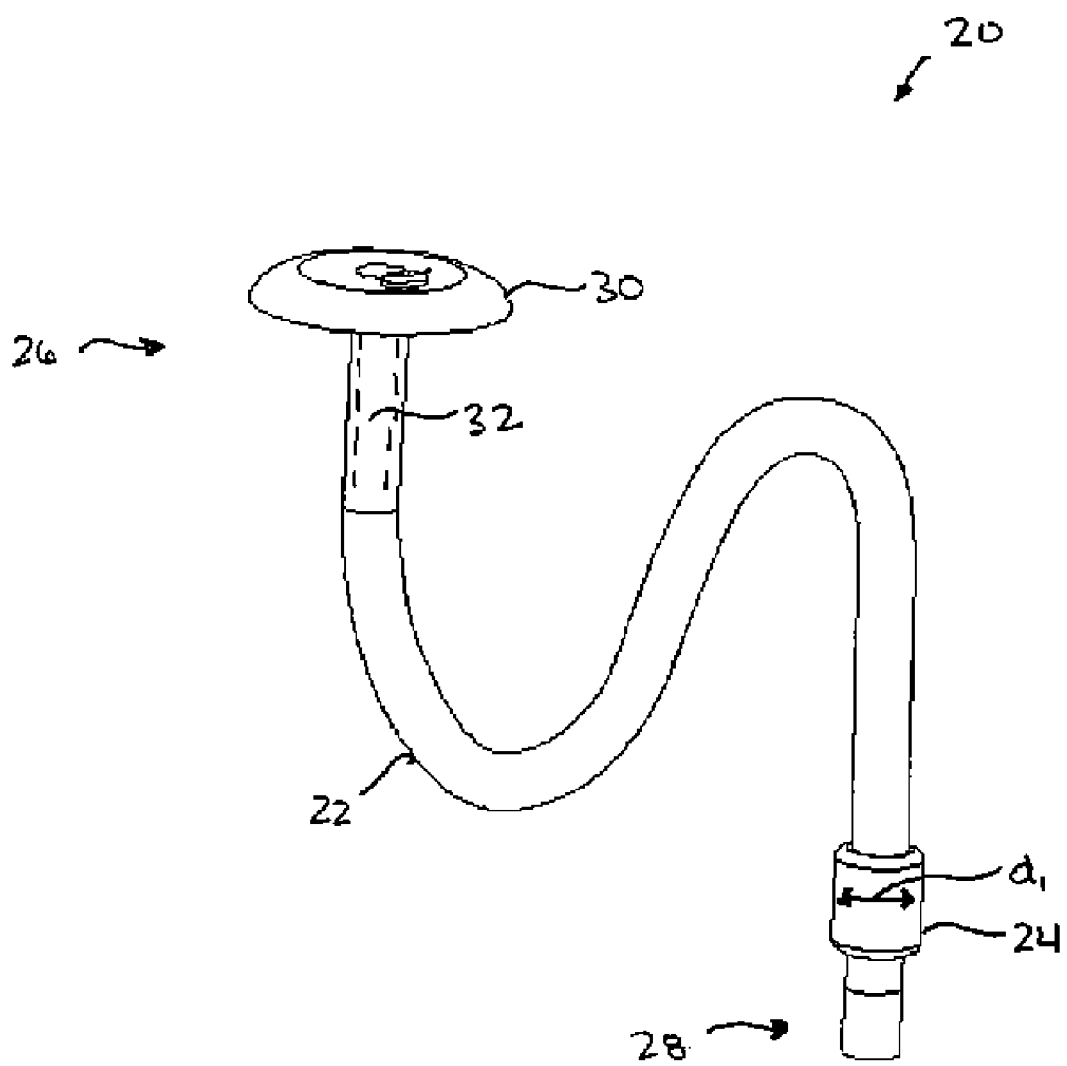
FIG. 1A is a perspective view of one embodiment of a PEG tube having an electrically expandable element in an unexpanded state.
Figure 1B:
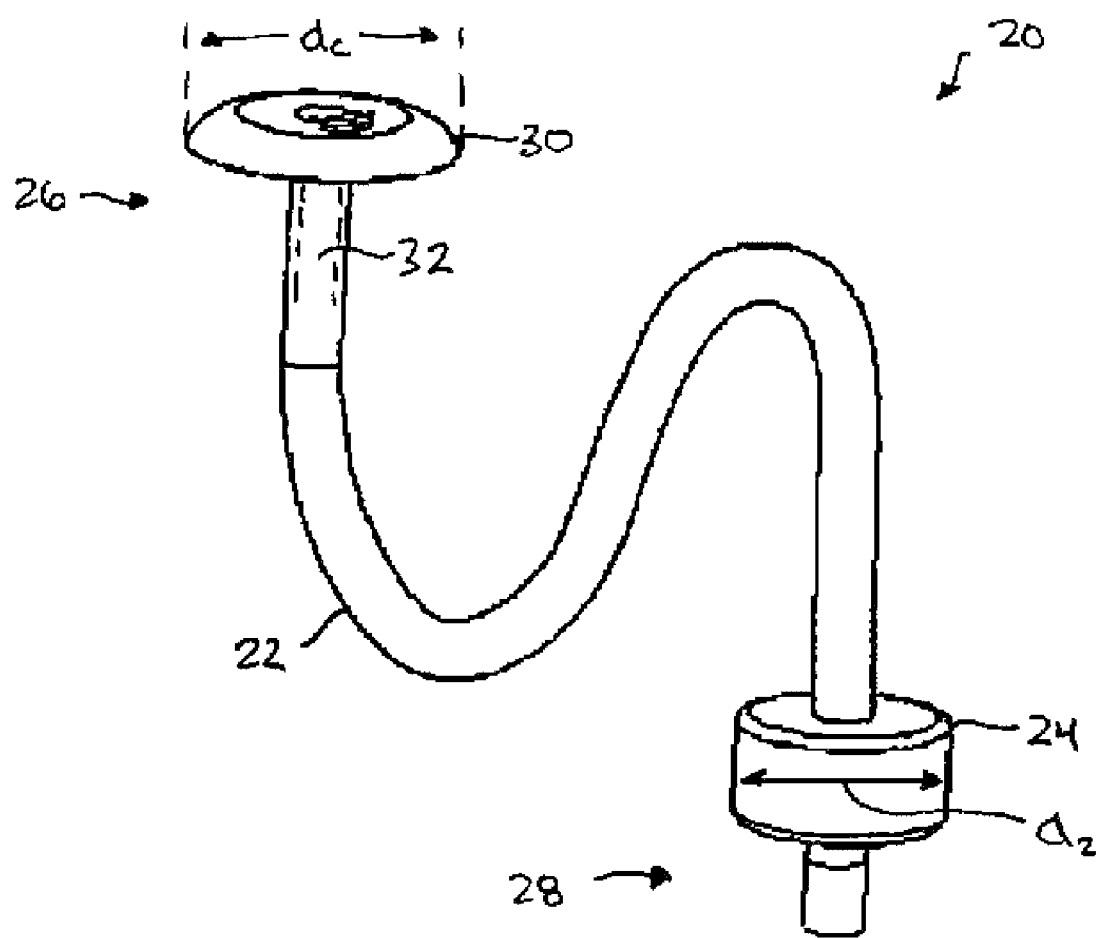
FIG. 1B is perspective view of the PEG tube of FIG. 1A showing the electrically expandable element in an expanded state.

FIGS. 1A and 1B illustrate one exemplary embodiment of a PEG tube 20. As illustrated, the PEG tube 20 generally includes an elongate member 22 and an electrically expandable element 24 coupled to the elongate member 22. The elongate member 22 can have a variety of configurations but in the illustrated embodiment it has a generally elongate shape with proximal and distal ends 26, 28 having an inner lumen 32 extending therebetween. The length of the elongate member 22 can vary depending on the intended use, but in an exemplary embodiment the elongate member 22 has a length that is adapted to allow the distal end 28 of the elongate member 22 to be positioned within a patient's stomach, while the proximal end 26 remains outside of the body to provide access through the lumen 32 for the introduction and/or removal of fluids, or optionally medical devices. By way of non-limiting example, the length can be in the range of about 12 inches to 18 inches. The elongate member 22 can also be formed from a variety of materials. For example, the elongate member 22 can be formed from a substantially flexible material that, upon insertion into a lumen of a patient's body, allows the elongate member 22 to be manipulated into a desired orientation.

The proximal end 26 of the elongate member 22 can have a variety of configurations, and it can include features to facilitate grasping of the device 20, and/or to prevent passage of the proximal end 26 through tissue. For example, in one embodiment the proximal end 26 of the elongate member 22 can include an external structure, such as a flange or cap member 30 formed thereon, as shown. The cap member 30 can facilitate grasping of the device, and it can also be used to prevent passage of the proximal end 26 into the patients body. In particular, the cap member 30 can have a diameter $d_c$ that is sufficient to allow the cap member 30 to rest against a tissue surface without passing through the tissue. The cap member 30 can be fixedly attached to or integrally formed with the proximal end 26, or it can be slideably coupled to the proximal end 26 of the elongate member 22 to allow the cap member 30 to be positioned as desired. Where the cap member 30 is slidably coupled to the elongate member 22, the cap member 30 can be slid and positioned at a desired location relative to a tissue surface to maintain the elongate member 22 at a particular insertion depth. Alternatively, a fixation device, such as a clamp or external support, can be used to grasp and maintain the elongate member 22 in a desired position once implanted.

As previously indicated, the PEG tube 20 can also include one or more electrically expandable elements that are adapted to change dimensions when energy is delivered thereto. In the embodiment shown in FIGS. 1A and 1B, the PEG tube 20 includes a single electrically expandable element 24 disposed on the distal end 28 thereof. The PEG tube 20 can, however, include any number of electrically expandable elements attach thereto at a variety of locations. The electrically expandable element 24 can also have a variety of configurations, but in an exemplary embodiment the electrically expandable element 24 is formed from an electroactive polymer material.

Electroactive polymers (EAPs), also referred to as artificial muscles, are materials that exhibit piezoelectric, pyroelectric, or electrostrictive properties in response to electrical or mechanical fields. In particular, EAPs are a set of conductive doped polymers that change shape when an electrical voltage is applied. The conductive polymer can be paired with some form of ionic fluid or gel using electrodes. Upon application of a voltage potential to the electrodes, a flow of ions from the fluid/gel into or out of the conductive polymer can induce a shape change of the polymer. Typically, a voltage potential in the range of about 1V to 4 kV can be applied depending on the particular polymer and ionic fluid or gel used. It is important to note that EAPs do not change volume when energized, rather they merely expand in one direction and contract in a transverse direction.

One of the main advantages of EAPs is the possibility to electrically control and fine-tune their behavior and properties. EAPs can be deformed repetitively by applying external voltage across the EAP, and they can quickly recover their original configuration upon reversing the polarity of the applied voltage. Specific polymers can be selected to create different kinds of moving structures, including expanding, linear moving, and bending structures. The EAPs can also be paired to mechanical mechanisms, such as springs or flexible plates, to change the effect of the EAP on the mechanical mechanism when voltage is applied to the EAP. The amount of voltage delivered to the EAP can also correspond to the amount of movement or change in dimension that occurs, and thus energy delivery can be controlled to effect a desired amount of change.

There are two basic types of EAPs and multiple configurations for each type. The first type is a fiber bundle that can consist of numerous fibers bundled together to work in cooperation. The fibers typically have a size of about 30-50 microns. These fibers may be woven into the bundle much like textiles and they are often referred to as EAP yarn. In use, the mechanical configuration of the EAP determines the EAP actuator and its capabilities for motion. For example, the EAP may be formed into long strands and wrapped around a single central electrode. A flexible exterior outer sheath will form the other electrode for the actuator as well as contain the ionic fluid necessary for the function of the device. When voltage is applied thereto, the EAP will swell causing the strands to contract or shorten. An example of a commercially available fiber EAP material is manufactured by Santa Fe Science and Technology and sold as PANION™ fiber and described in U.S. Pat. No. 6,667,825, which is hereby incorporated by reference in its entirety.

Figure 2A:
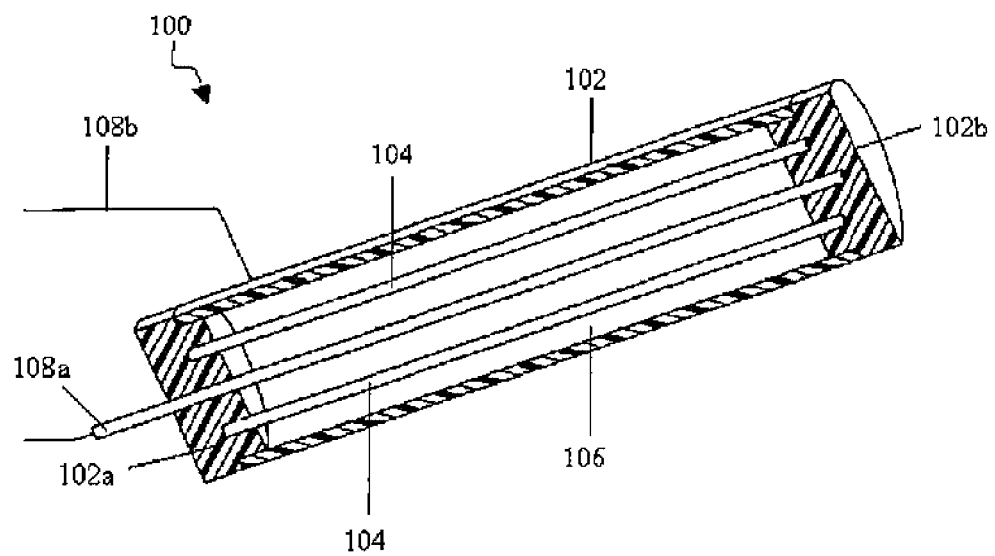
FIG. 2A is a cross-sectional view of a prior art fiber bundle type electroactive polymer (EAP) actuator.
Figure 2B:
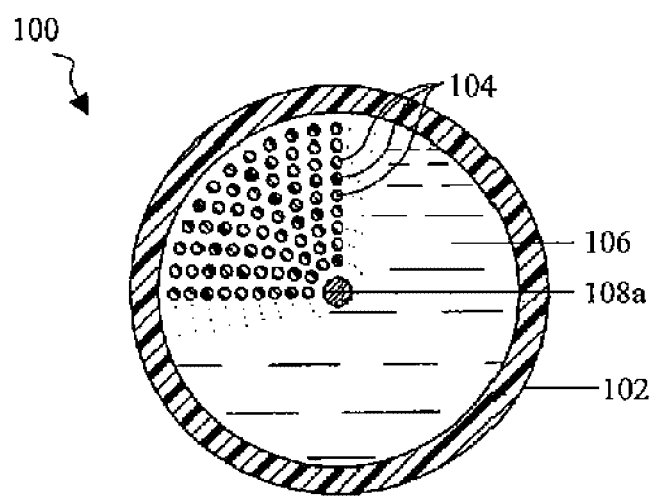
FIG. 2B is a radial cross-sectional view of the prior art actuator shown in FIG. 2A.

FIGS. 2A and 2B illustrate one exemplary embodiment of an EAP actuator 100 formed from a fiber bundle. As shown, the actuator 100 generally includes a flexible conductive outer sheath 102 that is in the form of an elongate cylindrical member having opposed insulative end caps 102a, 102b formed thereon. The conductive outer sheath 102 can, however, have a variety of other shapes and sizes depending on the intended use. As is further shown, the conductive outer sheath 102 is coupled to a return electrode 108a, and an energy delivering electrode 108b extends through one of the insulative end caps, e.g., end cap 102a, through the inner lumen of the conductive outer sheath 102, and into the opposed insulative end cap, e.g., end cap 102b. The energy delivering electrode 108b can be, for example, a platinum cathode wire. The conductive outer sheath 102 can also include an ionic fluid or gel 106 disposed therein for transferring energy from the energy delivering electrode 108b to the EAP fibers 104, which are disposed within the outer sheath 102. In particular, several EAP fibers 104 are arranged in parallel and extend between and into each end cap 102a, 102b. As noted above, the fibers 104 can be arranged in various orientations to provide a desired outcome, e.g., radial expansion or contraction, or bending movement. In use, energy can be delivered to the actuator 100 through the active energy delivery electrode 108b and the conductive outer sheath 102 (anode). The energy will cause the ions in the ionic fluid to enter into the EAP fibers 104, thereby causing the fibers 104 to expand in one direction, e.g., radially such that an outer diameter of each fiber 104 increases, and to contract in a transverse direction, e.g., axially such that a length of the fibers decreases. As a result, the end caps 102a, 102b will be pulled toward one another, thereby contracting and decreasing the length of the flexible outer sheath 102.

Another type of EAP is a laminate structure, which consists of one or more layers of an EAP, a layer of ionic gel or fluid disposed between each layer of EAP, and one or more flexible conductive plates attached to the structure, such as a positive plate electrode and a negative plate electrode. When a voltage is applied, the laminate structure expands in one direction and contracts in a transverse or perpendicular direction, thereby causing the flexible plate(s) coupled thereto to shorten or lengthen, or to bend or flex, depending on the configuration of the EAP relative to the flexible plate(s). An example of a commercially available laminate EAP material is manufactured by Artificial Muscle Inc, a division of SRI Laboratories. Plate EAP material, referred to as thin film EAP, is also available from EAMEX of Japan.

Figure 3A:
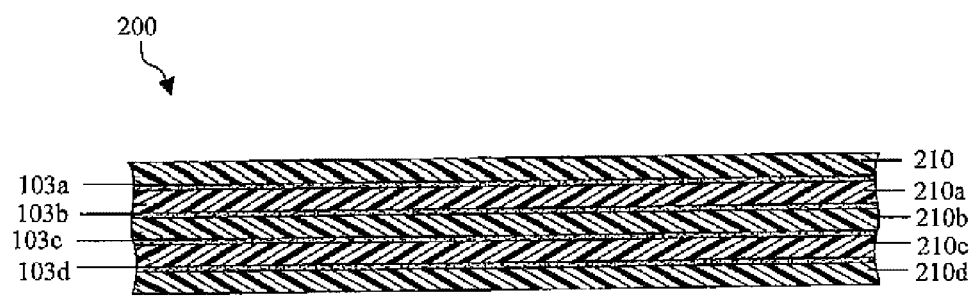
FIG. 3A is a cross-sectional view of a prior art laminate type EAP actuator having multiple EAP composite layers.
Figure 3B:
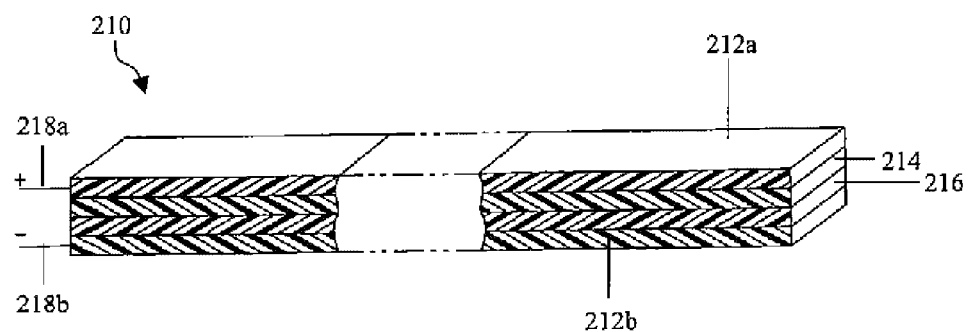
FIG. 3B is a perspective view of one of the composite layers of the prior art actuator shown in FIG. 3A.

FIGS. 3A and 3B illustrate an exemplary configuration of an EAP actuator 200 formed from a laminate. Referring first to FIG. 3A, the actuator 200 can include multiple layers, e.g., five layers 210, 210a, 210b, 210c, 210d are shown, of a laminate EAP composite that are affixed to one another by adhesive layers 103a, 103b, 103c, 103d disposed therebetween. One of the layers, i.e., layer 210, is shown in more detail in FIG. 3B, and as shown the layer 210 includes a first flexible conductive plate 212a, an EAP layer 214, an ionic gel layer 216, and a second flexible conductive plate 212b, all of which are attached to one another to form a laminate composite. The composite can also include an energy delivering electrode 218a and a return electrode 218b coupled to the flexible conductive plates 212a, 212b, as further shown in FIG. 3B. In use, energy can be delivered to the actuator 200 through the active energy delivering electrode 218a. The energy will cause the ions in the ionic gel layer 216 to enter into the EAP layer 214, thereby causing the layer 214 to expand in one direction and to contract in a transverse direction. As a result, the flexible plates 212a, 212b will be forced to flex or bend, or to otherwise change shape with the EAP layer 214.

Returning to FIGS. 1A and 1B, either type of actuator can be used to form the electrically expandable element 24, however in an exemplary embodiment the electrically expandable element 24 is formed using an EAP laminate, or a composite EAP formed from multiple laminate layers. The electrically expandable element 24 can be formed by rolling the EAP laminate around the elongate member 22 of the PEG tube 20. An adhesive or other mating technique can be used to attach the electrically expandable element 24 to the elongate member 22. While not shown, the expandable element 24 can be disposed within the inner lumen 32 of the elongate member 22, or alternatively the expandable element 24 can be integrally formed with the elongate member 22. The position of the expandable element 24 relative to the longitudinal axis of the elongate member 22 can also vary. For example, the expandable element 24 can be positioned around the distal-most end of the elongate member 22, or it can be positioned at a location proximal to the distal-most end, as shown in FIGS. 1A and 1B.

In use the orientation of the electrically expandable element 24 can be configured to allow the expandable element 24 to radially expand and axially contract upon the application of energy thereto. In particular, when energy is delivered to the electrically expandable element 24, the electrically expandable element 24 can increase from an initial diameter $d_1$ in an unexpanded position (e.g., in the absence of electrical energy), as shown in FIG. 1A, to an increased diameter $d_2$ in an expanded position, as shown in FIG. 1B. The dimensional change in the expandable element 24 will allow the expandable element 24 to function as an anchor, engaging tissue to prevent passage thereof through an opening formed in the tissue. A person skilled in the art will appreciate that various techniques can be used to deliver energy to the electrically expandable element 24. For example, the expandable element 24 can be coupled to a return electrode and a delivery electrode that is adapted to communicate energy from a power source to the actuator. The electrodes can extend through the inner lumen 32 formed in the elongate member 22, be embedded in the sidewalls of the elongate member 22, or they can extend along an external surface of the elongate member 22. The electrodes can couple to a battery source disposed within a housing coupled to or formed in the proximal end 26 of the tube 20, or they can extend through an electrical cord extending from the proximal end 26 of the tube 20 and adapted to couple to an electrical outlet.

Figure 4:
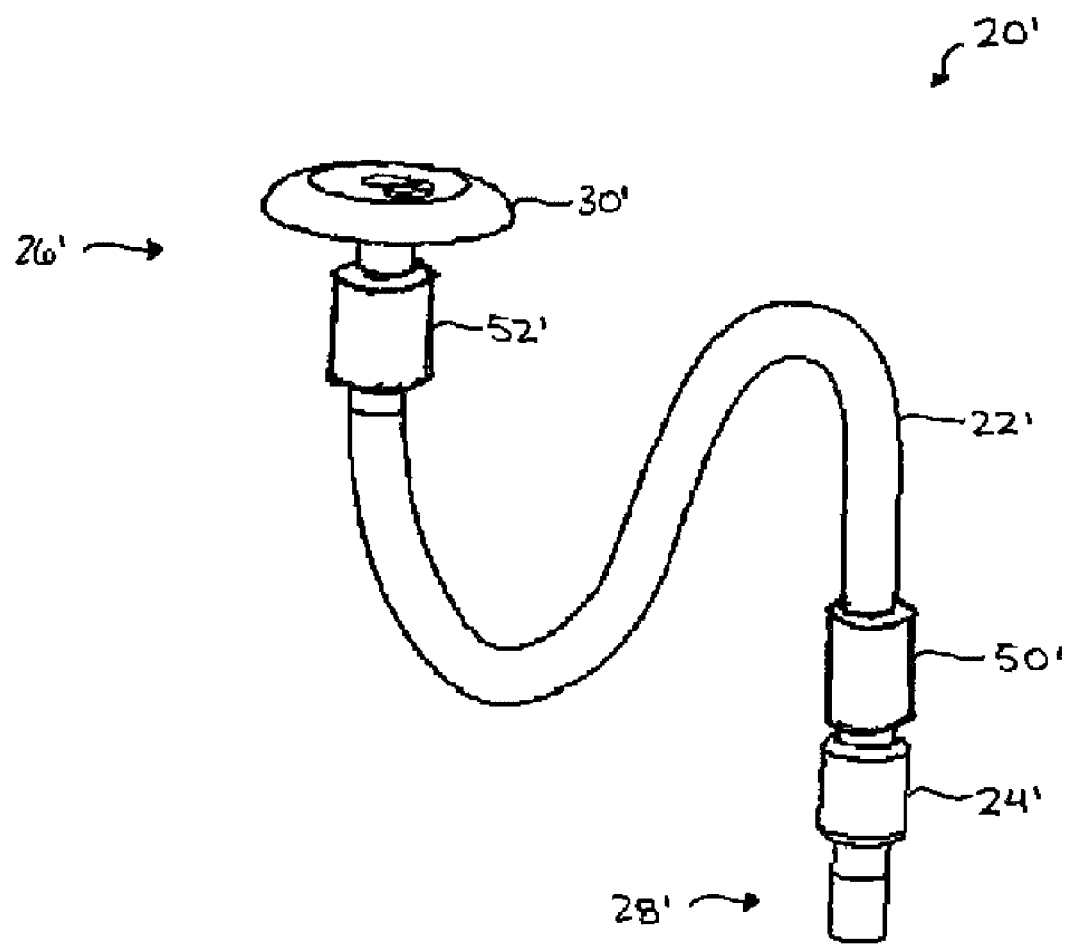
FIG. 4 is a perspective view of another embodiment of a PEG tube having multiple electrically expandable elements disposed on an elongate member.

While the PEG tube 20 shown in FIGS. 1A and 1B has only one electrically expandable element 24, as previously indicated the PEG tube 20 can include any number of electrically expandable elements located at various positions along the elongate member 22. By way of non-limiting example, FIG. 4 illustrates another embodiment of a PEG tube 20' having three electrically expandable elements 24', 50', 52'. In particular, a first expandable element 24' is coupled to the distal end 28' of the elongate member 22', and a second expandable 50' is coupled to the distal end 28' of the elongate member 22' at a location proximal to the first electrically expandable element 24'. Such a configuration allows the first and second expandable elements 24', 50' to be positioned on opposed sides of a tissue and to be electrically expanded to maintain the distal end 28' of the elongate member 22' in a substantially fixed position relative to the tissue. The PEG tube 20' can also optionally or alternatively include a third expandable element 52', which can be coupled to the proximal end 26' of the elongate member 22'. In the illustrated embodiment, the third expandable element 52' is positioned just distal to the cap member 30'. Such a configuration allows the expandable element 52' and the cap member 30' to engage tissue positioned therebetween.

FIGS. 5A-5F illustrate one exemplary method for using a PEG tube, such as PEG tube 20 of FIGS. 1A and 1B. As indicated above, in an exemplary embodiment the PEG tube 20 can be use to deliver and/or withdraw fluids from a stomach pouch, such as following a gastric bypass procedure. A person skilled in the art will appreciate that the PEG tube 20 can also be used in a variety of other medical procedures.

Figure 5A:
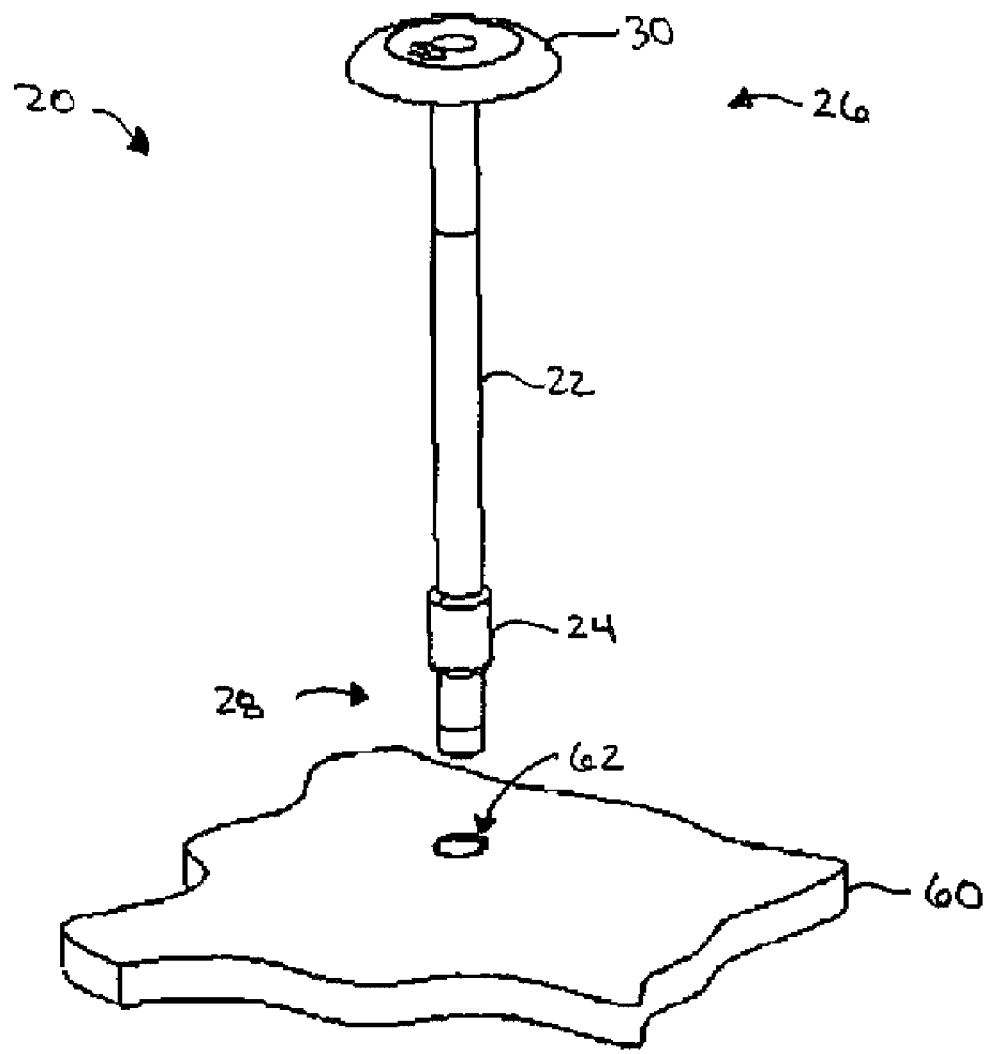
FIG. 5A illustrates the PEG tube of FIG. 1 positioned relative to a proximal tissue.
Figure 5B:
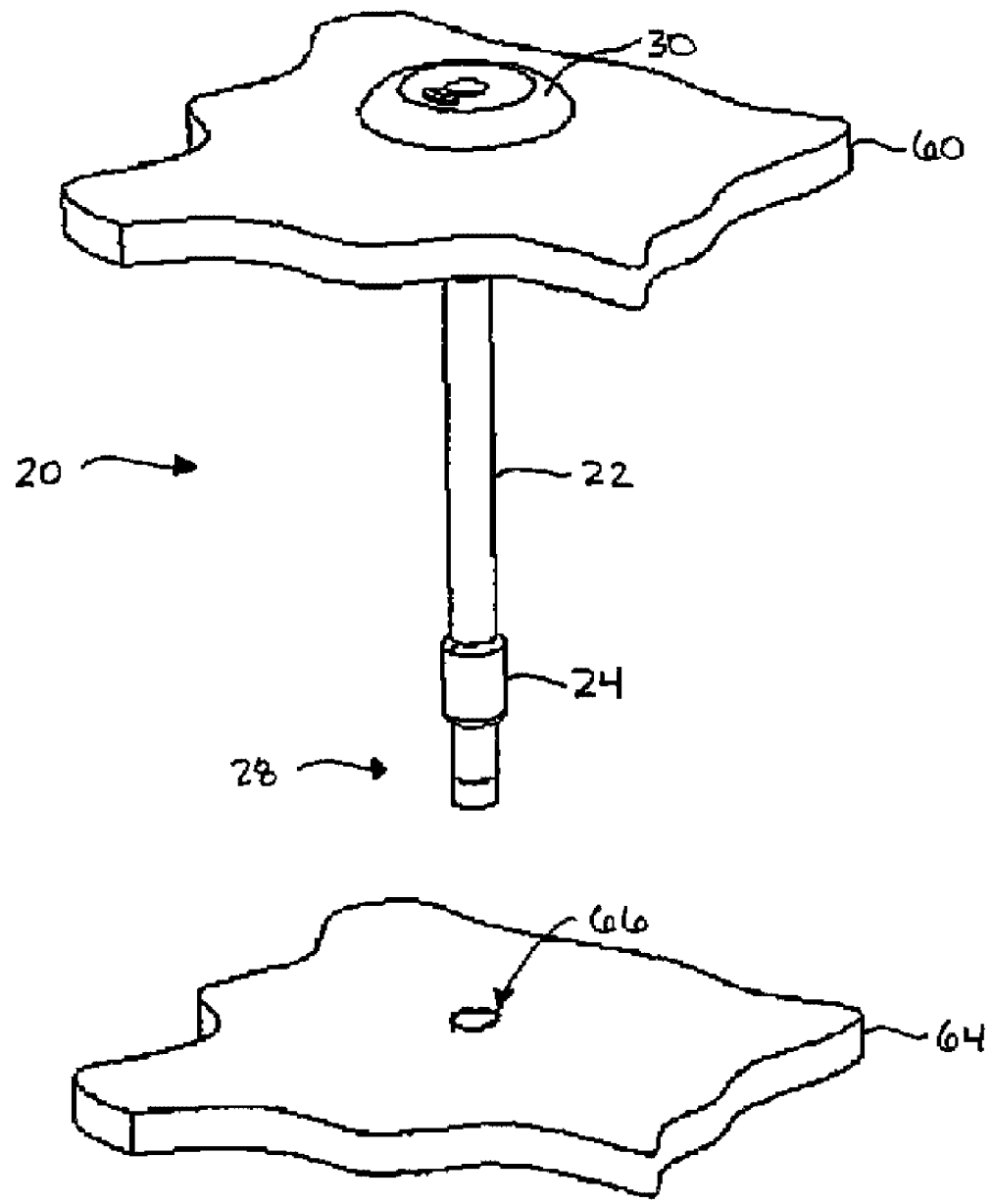
FIG. 5B illustrates the PEG tube of FIG. 5A inserted through an opening formed in the proximal tissue and positioned adjacent to a distal tissue.
Figure 5C:
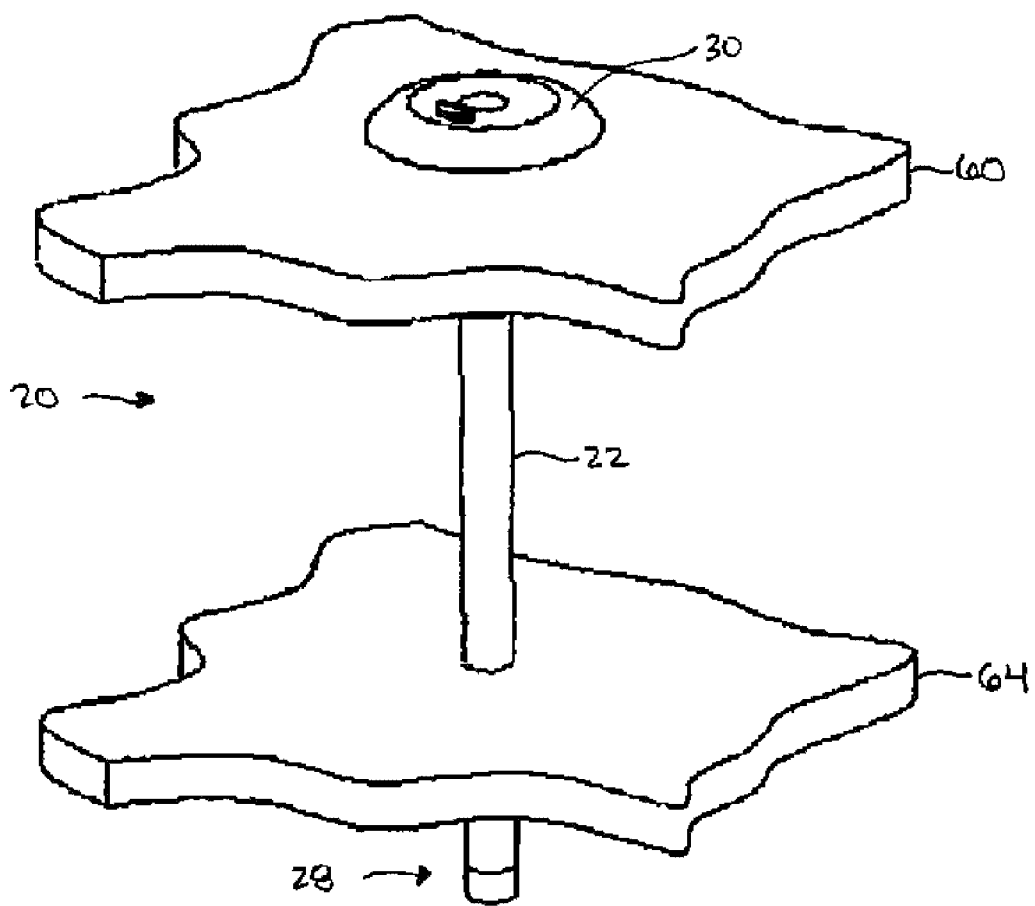
FIG. 5C illustrates the PEG tube of FIG. 5B with the distal end of the device inserted through an opening formed in the distal tissue.

During a PEG tube implantation procedure, a first opening 62 can be formed in a first tissue, e.g., the abdominal wall 60 of a patient, as shown in FIG. 5A. With the electrically expandable element 50 in the initial, radially contracted configuration (e.g., non-electrically activated), the elongate member 22 can be advanced into and through the opening 62, as shown in FIG. 5B. The distal end 28 of the PEG tube 20 is then passed through a second opening 66 that is formed in a second tissue, e.g., the stomach wall 64 of the patient, as shown in FIG. 5C. Laparoscopic graspers can be used to manipulate the elongate member 22 relative to the stomach wall 64 to guide the distal end 28 through the opening 66 in the stomach wall 64 and into the stomach pouch.

Figure 5D:
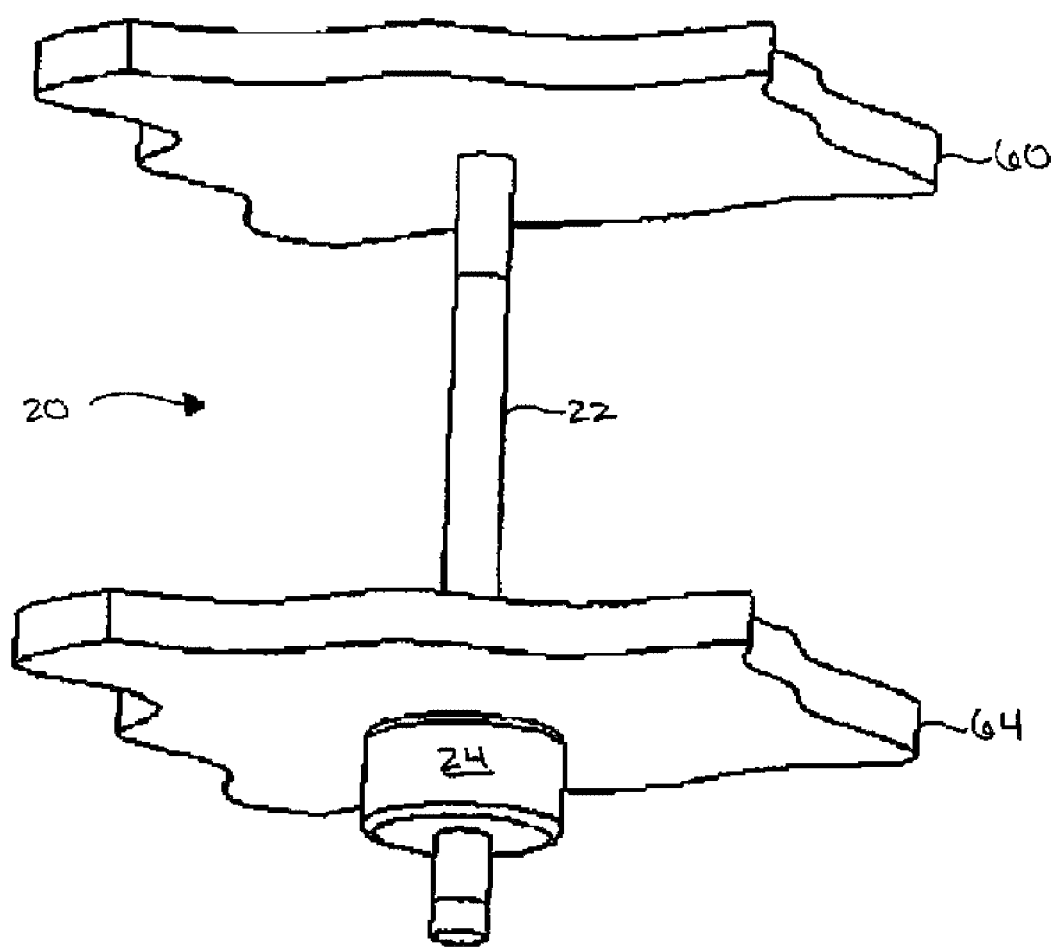
FIG. 5D illustrates the PEG tube of FIG. 5C having an expandable element expanded to engage the distal tissue.
Figure 5E:
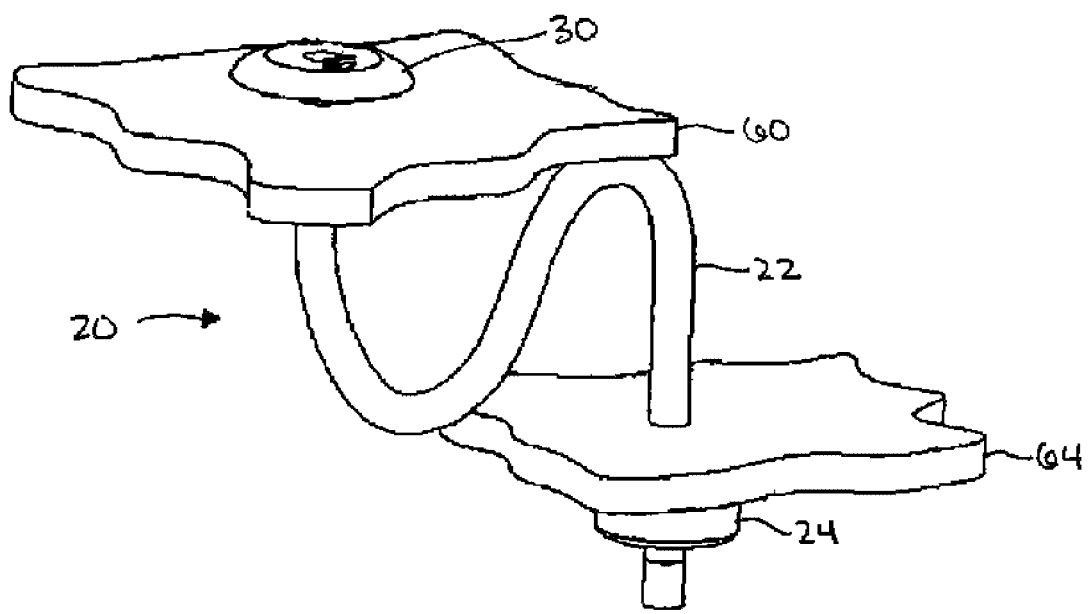
FIG. 5E illustrates the PEG tube of FIG. 5D, showing the end cap positioned adjacent to the proximal tissue and the expandable element expanded to engage the distal tissue.

Once the electrically expandable element 24 is inserted into the stomach pouch, electrical energy can be delivered to the electrically expandable element 24 to cause a change in the geometry of the element 24, and more preferably to cause the expandable element 24 to radially expand and thereby engage the tissue 64 (e.g., to limit or prevent passage of the electrically expandable element 24 through the opening 66 in the stomach wall 64), as shown in FIG. 5D. In an exemplary embodiment, the expandable element 24 is expanded to a desired size by limiting the amount of energy delivered thereto, as the amount of energy can correlate to the amount of expansion that occurs. Energy delivery can be controlled using, for example, a controller 36 (e.g., a button, knob, or dial) coupled to the energy source. FIG. 5E illustrates the device 20 fully implanted. Energy delivery is maintained to maintain the distal end 28 of the elongate member 22 within the stomach, and the end cap 30 at the proximal end 26 of the elongate member 22 rests against the external tissue surface 60.

Figure 5F:
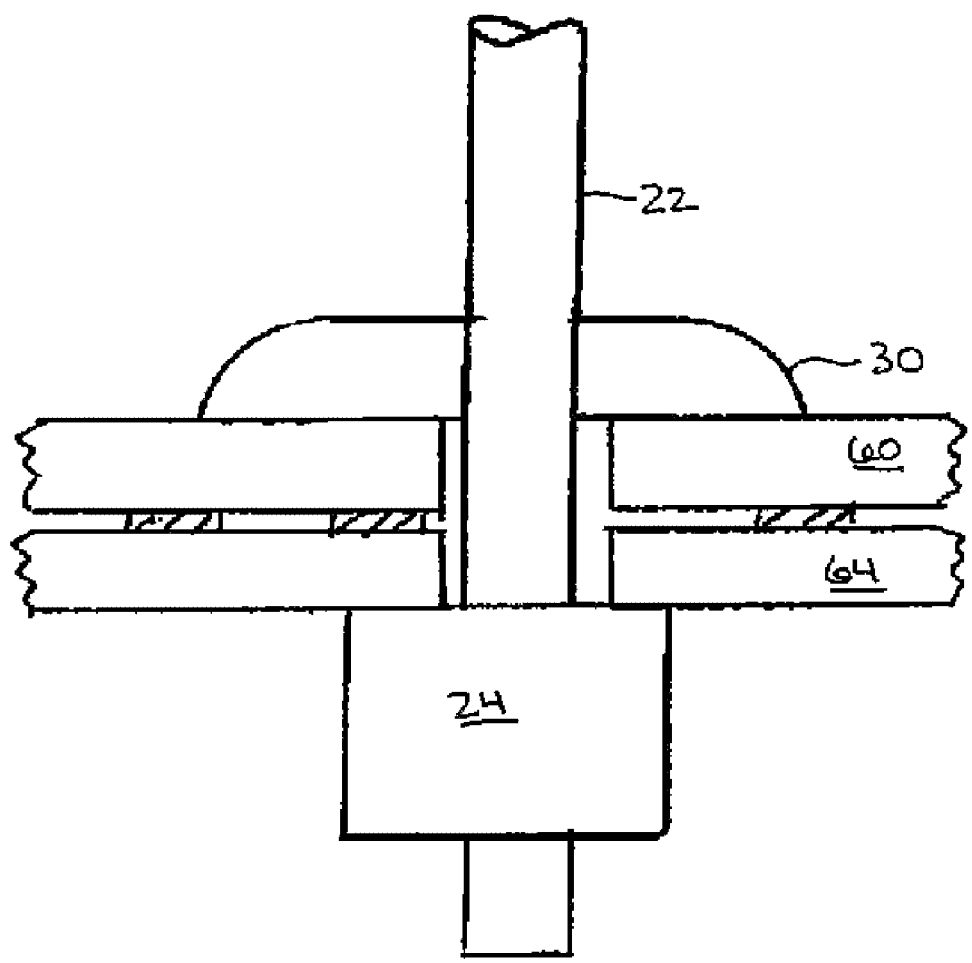
FIG. 5F illustrates a portion of the PEG tube of FIG. 5E moved to position the distal tissue in proximity to the proximal tissue.

In another embodiment, once the PEG tube 20 has been implanted within a stomach pouch of a patient, the PEG tube 20 can be used to adjust a position of the stomach pouch within the patient. For example, the PEG tube 20 can be used to move the stomach pouch wall 64 in proximity to the abdominal wall 64 to allow the stomach pouch wall 64 to attach to the abdominal wall 64. As shown in FIG. 5F, this can be achieved by pulling the elongate member 22 in a proximal direction to cause the expanded element 24 to engage and move the stomach wall 64 in proximity to (e.g., in contact with) the abdominal wall 60. The proximal end 26 of the elongate member 22 can then be clamped or attached to a support to maintain the PEG tube 20 in the retracted position. Eventually, adhesions will form between the walls 60, 64 to permanently secure the stomach pouch wall 64 to the abdominal wall 64.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A percutaneous endoscopic gastrostomy (PEG) tube, comprising:

an elongate member having a proximal end adapted to be positioned adjacent to a tissue surface, a distal end adapted to be inserted through tissue and into a body lumen, and an inner lumen extending between the proximal and distal ends and adapted to allow fluid flow therethrough; and an electrically expandable element coupled to the distal end of the elongate member and extending circumferentially therearound such that opposed ends of the electrically expandable element contact and abut and configured to change dimensionally upon delivery of electrical energy thereto.

2. The PEG tube of claim 1, wherein the electrically expandable element comprises an electroactive polymer actuator.

3. The PEG tube of claim 1, wherein the electrically expandable element has a diameter that is adapted to increase in correlation with an amount of energy delivered thereto.

4. The PEG tube of claim 1, wherein the electrically expandable element is configured to radially expand upon delivery of electrical energy thereto.

5. The PEG tube of claim 4, wherein the electrically expandable element comprises at least one electroactive polymer composite having at least one flexible conductive layer, an electroactive polymer layer, and an ionic gel layer.

6. The PEG tube of claim 1, further comprising a cap member coupled to the proximal end of the elongate member and adapted to limit passage of the elongate member through tissue.

7. The PEG tube of claim 4, wherein the cap member slideably couples to the elongate member.

8. The PEG tube of claim 1, wherein the electrically expandable element comprises a first electrically-expandable element, and the PEG tube further comprises a second electrically expandable element coupled to the distal end of the elongate member and configured to change dimensionally upon delivery of electrical energy thereto, the second electrically expandable element being positioned just proximal to the first electrically-expandable element such that the first and second electrically expandable elements are adapted to engage tissue therebetween when energy is delivered thereto.

9. The PEG tube of claim 1, wherein the electrically expandable element comprises a first electrically expandable element, and the PEG tube further comprises a second electrically expandable element coupled to the proximal end of the elongate member and configured to change dimensionally upon delivery of electrical energy thereto.

10. The PEG tube of claim 9, wherein the second expandable element is positioned distal to a cap member coupled to the proximal end of the elongate member.

11. A percutaneous endoscopic gastrostomy (PEG) tube, comprising:

a hollow elongate member having a proximal portion with a flange formed thereon and adapted to be positioned adjacent to a tissue surface, and a distal portion adapted to be inserted though tissue; and at least one electroactive polymer actuator extending circumferentially around the hollow elongate member such that opposed ends of the electroactive polymer actuator contact and abut and having a diameter that is adapted to be selectively increased when energy is delivered thereto to engage tissue.

12. The PEG tube of claim 11, wherein the at least one electroactive polymer actuator comprises an electroactive polymer composite having at least one flexible conductive layer, an electroactive polymer layer, and an ionic gel layer.

13. The PEG tube of claim 11, wherein at least one electroactive polymer actuator is coupled to the distal portion of the hollow elongate member.

14. A method for implanting a percutaneous endoscopic gastrostomy (PEG) tube, comprising:

inserting a distal portion of a PEG tube though tissue and into a body lumen to position an expandable element extending circumferentially around the distal portion of the PEG tube within the body lumen such that opposed ends of the expandable element contact and abut; and delivering energy to the expandable element to increase a diameter of the expandable element, thereby causing the expandable element to engage the body lumen.

15. The method of claim 14, wherein energy is delivered in an amount that correlates to a desired size of the expandable element.

16. The method of claim 14, wherein the tissue is the abdominal wall and the body lumen is in the stomach, and the method further comprises pulling a proximal portion of the PEG tube to move the stomach toward the abdominal wall.

17. The method of claim 16, further comprising delivering fluid to the stomach through the PEG tube.

18. The method of claim 16, further comprising removing fluid from the stomach through the PEG tube.

19. The method of claim 14, wherein the expandable element comprises an electroactive polymer.

* * * * *